United States Patent [19]

Neustadt

[11] 4,093,742

[45] June 6, 1978

[54] ANTI-HYPERTENSIVE POLYHALOISOPROPYL-SUBSTITUTED ARYLUREAS

[75] Inventor: Bernard R. Neustadt, West Orange, N.J.

[73] Assignee: Schering Corporation, Kenilworth, N.J.

[21] Appl. No.: 683,104

[22] Filed: May 4, 1976

Related U.S. Application Data

[63] Continuation-in-part of Ser. No. 528,603, Dec. 2, 1974, abandoned.

[30] Foreign Application Priority Data

Nov. 21, 1975 Switzerland .................. 15164/75

[51] Int. Cl.$^2$ .................. A61K 31/17; C07C 127/19
[52] U.S. Cl. .................. 424/322; 260/553 A; 260/571; 260/573; 260/574; 260/575; 260/576; 260/577; 260/578; 424/309; 424/311; 560/34; 560/251

[58] Field of Search ....... 260/488 CD, 553 A, 471 R; 560/34, 251; 424/309, 322, 311

[56] References Cited

U.S. PATENT DOCUMENTS

| 3,405,177 | 10/1968 | Jones | 260/575 |
|---|---|---|---|
| 3,594,418 | 7/1971 | Gilbert | 260/575 |
| 3,734,961 | 5/1973 | Englehart | 260/553 A |

FOREIGN PATENT DOCUMENTS 1,911,610  10/1970  Germany.

OTHER PUBLICATIONS

CA 80:104747s, (1974).
CA 72:90114d, (1968).

*Primary Examiner*—Daniel E. Wyman
*Assistant Examiner*—Thomas A. Waltz
*Attorney, Agent, or Firm*—Barbara L. Cowley Renda; Stephen B. Coan; Bruce M. Eisen

[57] ABSTRACT

Novel polyhaloisopropyl-substituted arylureas having potent antihypertensive properties are disclosed herein.

20 Claims, No Drawings

ANTI-HYPERTENSIVE POLYHALOISOPROPYL-SUBSTITUTED ARYLUREAS

This application is a continuation-in-part of my co-pending application Ser. No. 528,603, filed Dec. 2, 1974, now abandoned, which is hereby incorporated by reference.

This invention relates to novel polyhaloisopropyl-substituted arylureas which are useful in the treatment of mammalian hypertension. Used as such, they exhibit high potency with little or no depression of the central nervous system.

More particularly, this invention relates to arylureas of the formulae:

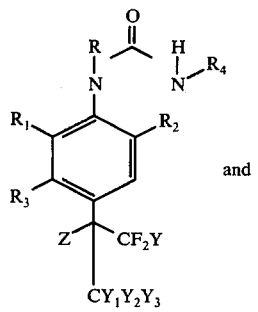

and

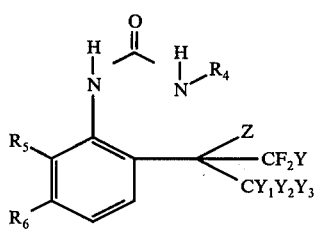

wherein $R_4$ is hydrogen or a methyl, ethyl, 2-chloroethyl or 2-bromoethyl group;

$R_1$, $R_2$ and $R_3$ are independently hydrogen, fluorine, chlorine, bromine, aminocarbonyl, lower alkyl, lower alkoxy, lower alkoxycarbonyl, hydroxy lower alkyl or nitro;

Y, $Y_1$, $Y_2$ and $Y_3$ are independently hydrogen, fluorine or chlorine;

Z is hydrogen, fluorine, chlorine, hydroxy, or lower alkanoyloxy;

R is hydrogen, alkyl having 1 to 4 carbon atoms, lower alkoxy lower alkyl or lower dialkoxy lower alkyl; and $R_5$ and $R_6$ are hydrogen or a lower alkyl group or $R_5$ and $R_6$ together complete a 5- or 6-carbon fused hydrocarbon ring which may be saturated or aromatic and which may be optionally substituted by a lower alkyl group.

The lower alkoxy groups referred to above contain 1 to 6 carbon atoms and are exemplified by such groups as methoxy, ethoxy, isopropoxy and the like. The lower alkanoyloxy groups contain 2 to 6 carbon atoms and are represented by acetoxy, propionyloxy and the like.

The lower alkyl groups likewise contain 1 to 6 carbon atoms and are exemplified by methyl, ethyl, n-propyl, isopropyl, isobutyl and the like. The lower dialkoxy lower alkyl groups are exemplified by such groups as dimethoxyethyl, diethoxyethyl, and ethylenedioxyethyl. The halogen atoms include chlorine, bromine and fluorine.

Within the scope of formulae (Ia) and (Ib) there are certain preferential embodiments. R is preferably an alkyl group containing 1 to 4 carbon atoms. $R_1$ and $R_2$ are preferably hydrogen or a lower alkyl group. $R_1$ and $R_2$ each being a lower alkyl group is a particularly preferred embodiment. Z is preferably a hydroxy group. $R_5$ and $R_6$ together are preferably a fused cyclohexyl ring.

Particularly preferred compounds of this invention are N-ethyl-N'-[4-(hexafluoro-2-hydroxy-2-propyl)-2,6-diisopropylphenyl]-N'-methylurea, N-(2-chloroethyl)-N'-[4-(hexafluoro-2-hydroxy-2-propyl)phenyl]-N'-methylurea and N-[2-(hexafluoro-2-hydroxy-2-propyl)-5,6,7,8-tetrahydro-1-naphthyl]-N'-methylurea.

The art discloses that polyhaloisopropyl-substituted anilines are known as intermediates to compounds possessing hypotensive activity, e.g., Jones, U.S. Pat. No. 3,405,177; Jones, U.S. Pat. No. 3,541,152; Gilbert, U.S. Pat. No. 3,594,418; Gilbert, U.S. Pat. No. 3,772,273; and Gilbert, J. Org. Chem., 30, 1001 (1965). However, no activity has been attributed to the intermediates themselves. Levitt, U.S. Pat. No. 3,499,083 discloses various other types of substituted arylureas. These ureas are described only as useful intermediates to oxazolines.

The compounds of formula (Ia) wherein Z is hydroxy may be prepared as outlined in Scheme A:

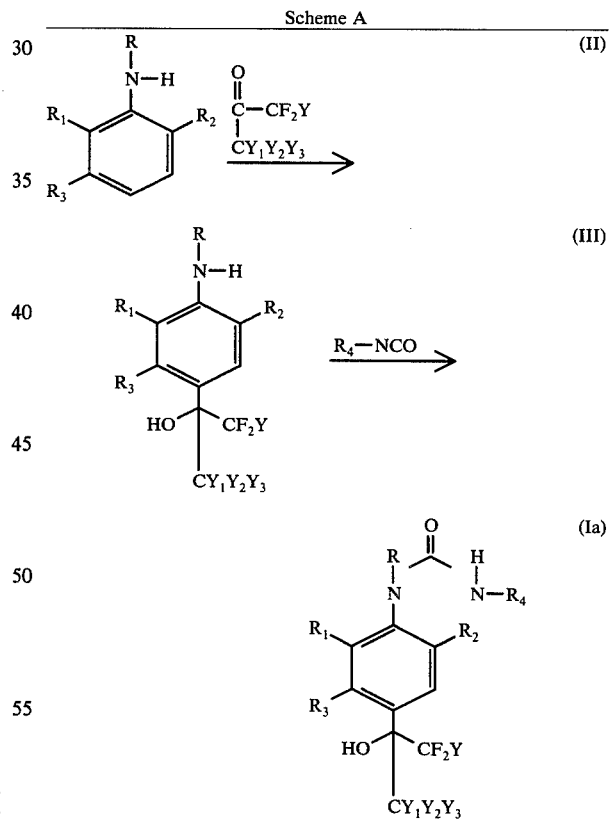

(R, $R_1$, $R_2$, $R_3$, $R_4$, Y, $Y_1$, $Y_2$ and $Y_3$ are as hereinbefore defined).

As shown in Scheme A, an N-substituted aniline of formula (II) is first reacted with a polyhalo ketone or hydrate thereof to form the corresponding 4-(polyhalo-2-hydroxy-2-propyl)-N-substituted aniline of formula (III). The entering polyhalo-2-hydroxy-2-propyl group occupies a position largely para to the amino group, although some ortho isomer is formed in some cases. The intermediate of formula (III) is then contacted with the appropriately substituted isocyanate or an alkali cyanate to form the desired urea of formula (Ia) wherein Z is a hydroxy group.

The compounds of formula (Ib) wherein Z is a hydroxy group may be prepared by similarly reacting an appropriate 2-(polyhalo-2-hydroxy-2-propyl)aniline of the formula (IV):

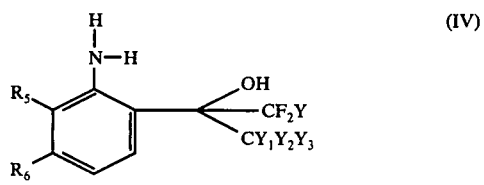

(IV)

wherein $R_5$, $R_6$, Y, $Y_1$, $Y_2$ and $Y_3$ are as hereinbefore defined, with the appropriately substituted isocyanate or an alkali cyanate to form the desired urea of formula (Ib) wherein Z is a hydroxy group. The starting materials of formula (IV) are prepared according to the method of Gilbert, *J. Org. Chem.*, 30, 1001 (1965).

The compounds of formulae (Ia) and (Ib) wherein Z is chlorine are prepared by contacting the corresponding compound wherein Z is hydroxy with a suitable chlorinating agent, e.g., thionyl chloride. For instance, N-[2-(hexafluoro-2-hydroxy-2-propyl)-5,6,7,8-tetrahydro-1-naphthyl]-N'-methylurea is conveniently converted to N-[2-(2-chloro-1,1,1,3,3,3-hexafluoro-2-propyl)-5,6,7,8-tetrahydro-1-naphthyl]-N'-methylurea in this manner. The use of a suitable fluorinating agent, e.g., sulfur tetrafluoride, according to the procedure of *J.A.C.S.*, 87, 2410 (1965) affords the analogous compound wherein Z is fluorine, i.e., N-[2-(heptafluoro-2-propyl)-5,6,7,8-tetrahydro-1-naphthyl]-N'-methylurea.

The compounds of formulae (Ia) and (Ib) wherein Z is hydrogen are obtained by hydrogenation of the corresponding compound wherein Z is chlorine. The use of a catalyst, particularly a catalyst such as palladium on charcoal, facilitates this reaction. Thus, N-[2-(2-chloro-1,1,1,3,3,3-hexafluoro-2-propyl)-5,6,7,8-tetrahydro-1-naphthyl]-N'-methylurea may be converted to N-[2-(1,1,1,3,3,3-hexafluoro-2-propyl)-5,6,7,8-tetrahydro-1-naphthyl]-N'-methylurea by this method.

Reaction of the compounds of formulae (Ia) and (Ib) wherein Z is hydroxy with the appropriate acid chloride affords the corresponding alkanoyloxy derivative. For instance, reaction of N-[2-(hexafluoro-2-hydroxy-2-propyl)-5,6,7,8-tetrahydro-1-naphthyl]-N'-methylurea with acetyl chloride yields N-[2-(2-acetoxyhexafluoro-2-propyl)-5,6,7,8-tetrahydro-1-naphthyl]-N'-methylurea.

The $R_2$ substituent of the compounds of formula (Ia) may alternatively be added after the urea has been formed by conventional methods. For instance, N-ethyl-N'-[4-(hexafluoro-2-hydroxy-2-propyl)phenyl]urea may be brominated to form N-ethyl-N'-[2-bromo-4-(hexafluoro-2-hydroxy-2-propyl)phenyl]urea, or nitrated to form N-ethyl-N'-[4-(hexafluoro-2-hydroxy-2-propyl)-2-nitrophenyl]urea.

An alternative method for the preparation of the compounds of formula (Ia) is that illustrated by Scheme B:

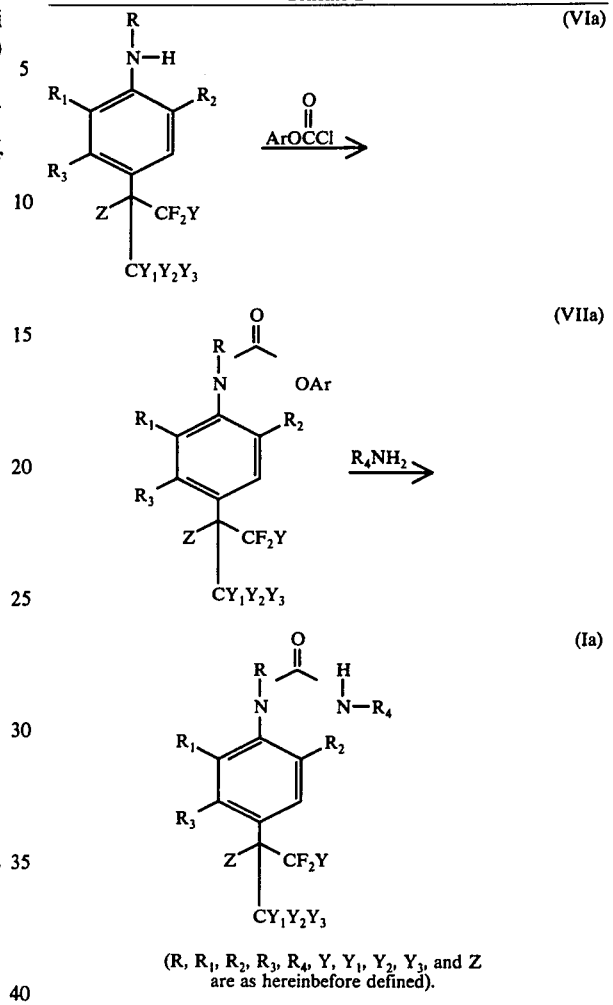

(R, $R_1$, $R_2$, $R_3$, $R_4$, Y, $Y_1$, $Y_2$, $Y_3$, and Z are as hereinbefore defined).

As shown in Scheme B, the polyhaloisopropylaryl aniline of formula (VIIa) is contacted with an aryl chloroformate, e.g., phenyl or p-nitrophenyl, to form the carbamate of formula (VIIa). This carbamate is in turn reacted with a primary amine to form the desired urea of formula (Ia).

An additional method useful for the preparation of the compounds of formula (Ia) involves contacting an intermediate of formula (VIa) with phosgene and isolating the chloroformamide of formula (VIIIa):

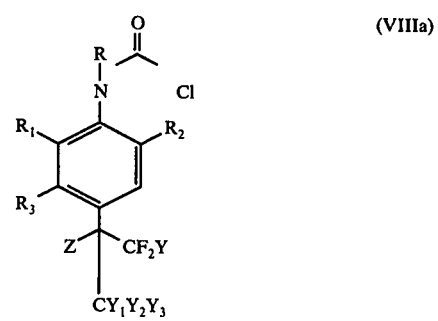

(VIIIa)

Reaction of this chloroformamide with the appropriate primary amine affords the desired compound of formula (Ia).

A number of agents are known for the treatment of hypertension. Certain of these; for example, reserpine, are effective in lowering the blood pressure in some patients but in other patients give rise to undesirable and well known side effects such as central nervous system depression.

The compounds of the present invention have been found to exhibit useful and potent anti-hypertensive activity. Further, representative compounds of the invention have been found to be particularly active as anti-hypertensive agents while avoiding or mitigating some of the deleterious side effects, such as the central nervous system depression associated with known antihypertensive agents. Based on laboratory tests, it is considered that the effective dosage (the $ED_{50}$) by oral administration for a compound of the present invention will typically lie within the range of from 0.05 to 20 mg/kg of mammalian weight. For the preferred compound, N-ethyl-N'-[4-(hexafluoro-2-hydroxy-2-propyl)-2,6-diisopropylphenyl]-N'-methylurea, the contemplated daily human dose is about 5 to 100 mg.

The required daily dosage may be administered in single or divided doses. The exact dose to be administered will, of course, be dependent upon where the compound in question lies within the above quoted dosage ranges and upon the age and weight of the subject mammal.

The compounds are administered orally. In any event, a suitable pharmaceutical carrier is employed, with the carrier selected according to the physical properties of the compound in the pharmaceutical composition. The carrier should not react chemically with the compound to be administered. The preparations containing the active ingredients may typically be in the form of tablets, capsules, syrups, elixirs or suspensions.

In treating certain patients with the compounds of this invention it may be desirable to include other pharmaceutically active ingredients in the same dosage unit. For example, in treating patients in whom salt and water retention is a problem, effective amounts of conventional diuretics can be incorporated, such as the thiazide diuretics, e.g., hydrochlorothiazide or trichloromethiazide. Similarly, in treating patients in whom tachycardia might be a problem, an effective amount of a pharmaceutically acceptable beta-blocking agent can be included, e.g., propranolol. The dosage unit could even contain a combination of a compound of this invention, e.g., N-ethyl-N'-[4-(hexafluoro-2-hydroxy-2-propyl)-2,6-diisopropylphenyl]-N'-methylurea, a diuretic, e.g., hydrochlorothiazide and a beta-blocker, e.g., propranolol.

The following examples describe in detail compounds and compositions illustrative of the present invention. It will be apparent to those skilled in the art that many modifications, both of materials and methods, may be practiced without departing from the purpose and intent of this disclosure.

EXAMPLE 1

4-(1,3-dichloro-2-hydroxytetrafluoro-2-propyl)-N-methyl aniline

Combine 21.4 g (0.2 mole) N-methyl aniline and 2.0 g of p-toluenesulfonic acid with 50 ml of toluene. Add dropwise 43.8 g (0.22 mole) 1,3-dichlorotetrafluoroacetone in 10 ml of toluene. Allow the reaction mixture to cool, concentrate partially, wash with 50 ml of 1N NaHCO$_3$, dry and concentrate to obtain 54 g of yellow solid. Recrystallize from diethyl ether, and hexane by dissolving in ether, adding hexane and evaporating off the ether to precipitate the solid to obtain 42 g of 4-(1,3-dichloro-2-hydroxytetrafluoro-2-propyl)-N-methyl aniline as a tan solid; m.p. 92°–94° C.

EXAMPLE 2

N-ethyl-N'-methyl-N'-[4-(1,3-dichloro-2-hydroxytetrafluoro-2-propyl)phenyl]urea

Combine 7.1 g (20 mmole) of 4-(1,3-dichloro-2-hydroxytetrafluoro-2-propyl)-N-methylaniline and 2.8 g (40 mmole) of ethyl isocyanate with 70 ml of Et$_2$O. After 16 hours, concentrate to obtain 8.6 g of white solid. Recrystallize from methanol and H$_2$O to obtain 7.8 g of N-ethyl-N'-methyl-N'-[4-(1,3-dichloro-2-hydroxytetrafluoro-2-propyl)phenyl]urea as a white solid; m.p. 155°–157° C.

EXAMPLE 3

Ethyl-5-(hexafluoro-2-hydroxy-2-propyl)anthranilate

Combine 16.5 g (0.1 mole) of ethyl anthranilate with 38.6 g (0.20 mole) of hexafluoroacetone sesquihydrate and reflux 24 hours. Add 19.3 g (0.1 mole) of hexafluoroacetone sesquihydrate to the reaction mixture and reflux for another 24 hours. Distill off the excess hexafluoroacetone hydrate in vacuo. Wash the residual solid with hexane and obtain 25 g of a pink solid. Recrystallize from ethanol and H$_2$O to obtain 20 g of ethyl-5-(hexafluoro-2-hydroxy-2-propyl)anthranilate as a pink solid; m.p. 115°–117° C.

EXAMPLE 4

N-ethyl-N'-[4-(hexafluoro-2-hydroxy-2-propyl)-2-(ethoxycarbonyl)phenyl]urea

Combine 4.3 g (13 mmole) of ethyl 5-(hexafluoro-2-hydroxy-2-propyl)anthranilate from the preceeding example, and 1.8 g (26 mmole) of ethyl isocyanate with 20 ml of Et$_2$O. Reflux for 5 days. Each day add another 1.8 g portion of ethyl isocyanate. Concentrate the reaction mixture to obtain 5.5 g of a white solid. Recrystallize from Et$_2$O-hexane to obtain 4.5 g. of N-ethyl-N'-[4-(hexafluoro-2-hydroxy-2-propyl)-2-(ethoxycarbonyl)phenyl]urea as a white solid; m.p. 144°–146° C.

EXAMPLE 5

N-ethyl-N'-[4-(hexafluoro-2-hydroxy-2-propyl)phenyl]urea

Combine 20.7 g (80 mmole) 4-(hexafluoro-2-hydroxy-2-propyl)-N-methylaniline (Gilbert, J. Org. Chem., 30, 1001 (1965)) and 11.3 g of ethyl isocyanate with 100 ml of diethyl ether and reflux for 16 hours. Concentrate the reaction mixture to obtain 26 g of white solid. Recrystallize from diethyl ether and hexane to obtain 24.5 g of N-ethyl-N'-[4-(hexafluoro-2-hydroxy-2-propyl)phenyl]urea; m.p. 178°–179° C.

EXAMPLE 6

N-(2-chloroethyl)-N'-[4-(hexafluoro-2-hydroxy-2-propyl)phenyl]-N'-methylurea

Combine 4.1 g (15 mmole) of 4-(hexafluoro-2-hydroxy-2-propyl)-N-methylaniline (Gilbert, J. Org. Chem., 30, 1001 (1965)) and 1.9 g (18 mmole) 2-chloroethyl isocyanate with 40 ml of Et$_2$O. Allow the mixture to stand overnight, concentrate to obtain 6 g of a beige solid. Recrystallize from Et$_2$O and hexane to obtain 5.5 g of N-(2-chloroethyl)-N'-[4-(hexafluoro-2-hydroxy-2- propyl)phenyl]-N'-methylurea as an off-white solid; m.p. 120°–121° C.

EXAMPLE 7

4-(hexafluoro-2-hydroxy-2-propyl)anilinoacetaldehyde dimethyl acetal

Combine 31.3 g (0.17 mole) of anilinoacetaldehydedimethylacetal and 1.7 g of p-toluenesulfonic acid with 200 ml of benzene. Bubble 32 g of (0.2 mole) hexafluoroacetone into the reaction mixture under nitrogen and then reflux for 20 minutes. Concentrate the reaction mixture and partition between hexane and 200 ml of 1N NaOH. Stir the NaOH with 400 ml of Et$_2$O and add 14.4 g of acetic acid. Wash the Et$_2$O with 250 ml of 1N NaHCO$_3$. Dry and treat the Et$_2$O with decolorizing charcoal. Concentrate to obtain 50 g of brown solid. Distill the brown solid at 0.1 mm Hg and collect 31 g of yellow oil between 140°–144° C which crystallizes upon cooling. Recrystallize from Et$_2$O and hexane to obtain 15 g of 4-(hexafluoro-2-hydroxy-2-propyl)anilinoacetaldehyde dimethyl acetal as a tan solid; m.p. 72°–74° C.

EXAMPLE 8

N'-(2,2-dimethoxyethyl-N'-[4-(hexafluoro-2-hydroxy-2-propyl)phenyl]-N-ethylurea

Combine 20.0 g (56 mmole) of [4-(hexafluoro-2-hydroxy-2-propyl)anilino]acetaldehyde dimethyl acetal (Example 7) and 1.5 g (22 mmole) ethyl isocyanate with 200 ml of diethyl ether. Allow the reaction mixture to stand overnight and then concentrate to obtain 25 g of a tan solid. Recrystallize from Et$_2$O and hexane to obtain 16 g of the title compound as a white solid; m.p. 138°–140° C.

EXAMPLE 9

N-ethyl-N'-[2-bromo-4-(hexafluoro-2-hydroxy-2-propyl)phenyl]urea

Combine 4.9 g (15 mmole) of N-ethyl-N'-[4-(hexafluoro-2-hydroxy-2-propyl)phenyl]urea (Example 4), 1.3 g (16.5 mmole) of NaOAc and 2.4 g (15 mmole) of bromine in 70 ml of acetic acid and stir for 20 hours. Pour the reaction onto 700 ml of ice water. Filter off the solid, dissolve in diethyl ether, dry and concentrate to obtain 5 g of foam. Treat the foam with CH$_2$Cl$_2$ to form a solid. Recrystallize from methanol and chloroform to obtain 3.5 g of N-ethyl-N'-[2-bromo-4-(hexafluoro-2-hydroxy-2-propyl)phenyl]urea as a white solid; m.p. 125°–127° C.

EXAMPLE 10

N-ethyl-N'-[4-(hexafluoro-2-hydroxy-2-propyl)-2-nitrophenyl]urea

Dissolve 12.0 g (36 mmole) of N-ethyl-N'-[4-(hexafluoro-2-hydroxy-2-propyl)phenyl]urea (Example 4) in 72 ml of concentrated H$_2$SO$_4$ and cool to below 5° C. Add dropwise a solution of 2.8 ml of concentrated HNO$_3$ in 24 ml of concentrated H$_2$SO$_4$ to the reactants and stir for 40 minutes. Pour the reactants onto 800 ml of ice water and stir. Filter off the yellow solid and take up in 400 ml of diethyl ether (Et$_2$O). Wash twice the Et$_2$O with 450 ml water. Dry and concentrate the Et$_2$O to obtain 13 g of yellow solid. Recrystallize from methanol and water to obtain 11 g of N-ethyl-N'-[4-(hexafluoro-2-hydroxy-2-propyl)-2-nitrophenyl]urea as a yellow solid; m.p. 169°–171° C.

EXAMPLE 11

Phenyl N-[4-(hexafluoro-2-hydroxy-2-propyl)phenyl]carbamate

Dissolve 10.3 g (40 mmole) of 4-(hexafluoro-2-hydroxy-2-propyl)aniline in 50 ml of CH$_3$CN. Add 7.8 g (50 mmole) of phenyl chloroformate followed by the dropwise addition of 3.1 g of dry pyridine in 10 ml of CH$_3$CN. Pour the reactants into 400 ml of H$_2$O. Filter off the solid, take up in Et$_2$O, wash with 200 ml of H$_2$O, dry and concentrate to obtain 16 g of white solid. Recrystallize from Et$_2$O and hexane to obtain 12.5 g of phenyl N-[4-(hexafluoro-2-hydroxy-2-propyl)phenyl]carbamate as a white solid; m.p. 192°–194° C.

EXAMPLE 12

N-[4-(hexafluoro-2-hydroxy-2-propyl)phenyl]urea

Combine 6.0 g (16 mmole) of phenyl N-[4-(hexafluoro-2-hydroxy-2-propyl)phenyl]carbamate (Example 12) and 65 ml of NH$_3$ saturated ethanol. After ½ hour, pour the reaction mixture into 150 ml of H$_2$O. Concentrate, cool to 0° C and filter off the white solid. Obtain 5.5 g of N-[4-(hexafluoro-2-hydroxy-2-propyl)phenyl]urea; m.p. 181°–183° C.

EXAMPLE 13

N-ethyl-N'-methyl-N'-[2,6-dimethyl-4-(hexafluoro-2-hydroxy-2-propyl)phenyl]urea

Heat at reflux for three hours 13.5 g of N,2,6-trimethylaniline (0.100 mole) and 40 g of hexafluoroacetone sesquihydrate (0.21 mole). Allow to cool, pour onto water. Collect the solid, dry and recrystallize from ether-hexane to give 27.9 g white solid; m.p. 143°–144° C. Dissolve 6 g of the product, N,2,6-trimethyl-4-(hexafluoro-2-hydroxy-2-propyl)aniline (20 mmole) and 5.4 g of ethyl isocyanate (80 mmole) in Et$_2$O. After 16 hours, concentrate and recrystallize the residual solid from etherhexane to give 6.2 g of a white solid; m.p. 178°–179° C.

EXAMPLE 14

N-[2-(hexafluoro-2-hydroxy-2-propyl)-5,6,7,8-tetrahydro-1-naphthyl]urea

To a solution of 2-(hexafluoro-2-hydroxy-2-propyl)-5,6,7,8-tetrahydro-1-naphthylamine (3.13 g, 10 mmole) in 50 ml HOAc add KCNO (4.05 g, 50 mmole). After ½ hour, pour onto water, stir and filter the solid. Dissolve the solid in Et$_2$O, dry, concentrate and recrystallize from Et$_2$O-hexane to give 1.50 g N-[2-(hexafluoro-2-hydroxy-2-propyl)-5,6,7,8-tetrahydro-1-naphthyl]urea as a white powder; m.p. 157°–159° C.

EXAMPLE 15

N-ethyl-N'-[5-(hexafluoro-2-hydroxy-2-propyl)-4-indanyl]urea

To 4-amino-5-(hexafluoro-2-hydroxy-2-propyl)indan (4.2g, 14 mmole, prepared from 4-aminoindan by the procedure of Gilbert, *J. Org. Chem.*, 30, 1001 (1965), m.p. 155°–8°) in 50 ml 4:1 Et$_2$O-hexane add ethyl isocyanate (1.3 g, 18mmole). After 1 hour filter the solid and dry to give 4.4 g N-ethyl-N'-[5-(hexafluoro-2-hydroxy-2-propyl)-4-indanyl]urea; m.p. 142°–143° C.

EXAMPLE 16

N-methyl-N-[4-(hexafluoro-2-hydroxy-2-propyl)-phenyl]carbamyl chloride

To a cold (10°) stirred mixture of 137 g (0.50 mole) 4-(hexafluoro-2-hydroxy-2-propyl)-N-methyl aniline in 500 ml Et$_2$O and 168 g (2.0 mole) NaHCO$_3$ in 500 ml H$_2$O add dropwise 500 g (0.6 mole) 12% phosgene in benzene over 1 hour. Add 500 ml Et$_2$O, separate the organic phase, dry, concentrate and wash the residue with hexane to give 167 g white solid; m.p. 152°–154°.

EXAMPLE 17

N-methyl-N-[4-(hexafluoro-2-hydroxy-2-propyl)-phenyl]urea

Saturate with NH$_3$ a solution of 6.7 g (20 mmole) N-methyl-N-[4-(hexafluoro-2-hydroxy-2-propyl)-phenyl]carbamyl chloride in 200 ml Et$_2$O. After 24 hours, wash the Et$_2$O with water, then 1N HCl. Dry, concentrate and recrystallize the solid from ether-hexane to give 5.0 g white solid; m.p. 181°–184°.

EXAMPLE 18

Repetition of the procedures detailed in the above examples using the appropriate starting materials affords the following compounds of this invention:

N-ethyl-N'-[4-(hexafluoro-2-hydroxy-2-propyl)-phenyl]-N'-methylurea;

N-ethyl-N'-[4-(hexafluoro-2-hydroxy-2-propyl)-2-methylphenyl]urea;

N,N'-diethyl-N'-[4-(hexafluoro-2-hydroxy-2-propyl)-phenyl]urea;

N-ethyl-N'-isopropyl-N'-[4-(hexafluoro-2-hydroxy-2-propyl)phenyl]urea;

N-ethyl-N'-[2-ethyl-4-(hexafluoro-2-hydroxy-2-propyl)phenyl]urea;

N-ethyl-N'-propyl-N'-[4-(hexafluoro-2-hydroxy-2-propyl)phenyl]urea;

N-ethyl-N'-methyl-N'-[4-(hexafluoro-2-hydroxy-2-propyl)-2-(methoxycarbonyl)phenyl]urea;

N-ethyl-N'-[4-(chloro-2-hydroxypentafluoro-2-propyl)phenyl]-N'-methylurea;

N-ethyl-N'-[2-chloro-4-(hexafluoro-2-hydroxy-2-propyl)phenyl]urea;

N-ethyl-N'-[4-(hexafluoro-2-hydroxy-2-propyl)-2-methylphenyl]-N'-methylurea;

N-ethyl-N'-[2-(methoxycarbonyl)-4-(hexafluoro-2-hydroxy-2-propyl)phenyl]urea;

N-ethyl-N'-[2-chloro-4-(hexafluoro-2-hydroxy-2-propyl)-6-methyl phenyl]urea;

N-(2-bromoethyl)-N'-[4-(hexafluoro-2-hydroxy-2-propyl)phenyl]-N'-methyl urea;

N-ethyl-N'-[4-(hexafluoro-2-hydroxy-2-propyl)-2-(2-propoxycarbonyl)phenyl]-N'-methylurea;

N-ethyl-N'-[4-(hexafluoro-2-hydroxy-2-propyl)-2-methyl-6-(methoxycarbonyl)phenyl]urea;

N-ethyl-N'-[4-(hexafluoro-2-hydroxy-2-propyl)-phenyl]-N'-(2-methoxyethyl)urea;

N-[4-(1,3-dichloro-2-hydroxytetrafluoro-2-propyl)-2,6-dimethylphenyl]-N'-ethyl urea;

N-(2-chloroethyl)-N'-[4-(hexafluoro-2-hydroxy-2-propyl)phenyl]urea;

N-ethyl-N'-methyl-N'-[4-(hexafluoro-2-hydroxy-2-propyl)-2-(hydroxymethyl)phenyl]urea;

N-ethyl-N'-[2-(hexafluoro-2-hydroxy-2-propyl)-1-naphthyl]-N'-methylurea;

N-ethyl-N'-[4-(2-hydroxypentafluoro-2-propyl)-phenyl]-N'-methylurea;

N-ethyl-N'-[4-(hexafluoro-2-hydroxy-2-propyl)-2-aminocarbonylphenyl]-N'-methylurea;

N-ethyl-N'-[4-(hexafluoro-2-hydroxy-2-propyl)-2-methyl-6-t-butylphenyl]urea;

N-(2-chloroethyl)-N'-methyl-N'-[2,6-dimethyl-4-(hexafluoro-2-hydroxy-2-propyl)phenyl]urea;

N-ethyl-N'-[4-(2-hydroxy-1,1,3-trichloro-1,3,3-trifluoro-2-propyl)phenyl]-N'-methyl urea;

N-ethyl-N'-(2-ethoxyethyl)-N'-[4-(hexafluoro-2-hydroxy-2-propyl)phenyl]urea;

N-[4-(hexafluoro-2-hydroxy-2-propyl)phenyl]-N-(2,2-diethoxyethyl)-N'-ethyl urea;

N,N'-diethyl-N-[4-(hexafluoro-2-hydroxy-2-propyl)-2,6-dimethylphenyl]urea;

N-(2-chloropropyl)-N'-methyl-N'-[4-(hexafluoro-2-hydroxy-2-propyl)phenyl]urea;

N-[5-bromo-2-(hexafluoro-2-hydroxy-2-propyl)-1-naphthyl]-N'-n-propyl urea;

N-[2,6-dimethyl-4-(2-hydroxy-1,1,3-trichloro-1,3,3-trifluoro-2-propyl)phenyl]-N'-ethyl urea;

N-ethyl-N'-[4-(hexafluoro-2-hydroxy-2-propyl)-2-methyl-1-naphthyl]urea;

N-[2-(hexafluoro-2-hydroxy-2-propyl)-1-naphthyl]-N'-methylurea;

N-[4-(1,3-dichloro-2-hydroxytetrafluoro-2-propyl)-2,6-diethylphenyl]-N'-ethyl urea;

N-2-(chloroethyl)-N'-[2-(hexafluoro-2-hydroxy-2-propyl)-1-naphthyl]urea;

N-ethyl-N'-[2,6-diethyl-4-(hexafluoro-2-hydroxy-2-propyl)phenyl]urea;

N-ethyl-N'-[4-(hexafluoro-2-hydroxy-2-propyl)-phenyl]-N'-[(1,3-dioxolan-2-yl)methyl]urea;

N-[7-methyl-2-(hexafluoro-2-hydroxy-2-propyl)-1-naphthyl]-N'-n-propyl urea;

N-ethyl-N'-[4-(hexafluoro-2-hydroxy-2-propyl)-2,6-diisopropylphenyl]-N'-methyl urea;

N-(2-chloroethyl)-N'-[4-(hexafluoro-2-hydroxy-2-propyl)phenyl]-N'-(n-propyl)urea;

N-ethyl-N'-methyl-N'-[2,6-dimethyl-4-(1,3-dichlorotetrafluoro-2-hydroxy-2-propyl)phenyl]urea;

N-ethyl-N'-[4-(hexafluoro-2-hydroxy-2-propyl)-2-methylphenyl]-N'-methylurea;

N-ethyl-N'-[2,6-dimethyl-4-(hexafluoro-2-hydroxy-2-propyl)phenyl]urea;

N-ethyl-N'-[2,6-diisopropyl-4-(hexafluoro-2-hydroxy-2-propyl)-phenyl]urea;

N-ethyl-N'-(2,2-dimethoxyethyl)-N'-[4-(hexafluoro-2-hydroxy-2-propyl)-2-methylphenyl]urea;

N-ethyl-N'-[5-(hexafluoro-2-hydroxy-2-propyl)-4-indanyl]urea;

N-[2-(1,3-dichlorotetrafluoro-2-hydroxy-2-propyl)-5,6,7,8-tetrahydro-1-naphthyl]-N'-methylurea;

N-[2-(hexafluoro-2-hydroxy-2-propyl)-6-n-propylphenyl]-N'-methylurea; and

N-[2-(hexafluoro-2-hydroxy-2-propyl)-6-isopropylphenyl]-N'-methylurea.

EXAMPLE 19

| Tablet Formulations | |
|---|---|
| Formulation I | Milligrams per Tablet |
| N-ethyl-N'-[4-(hexafluoro-2-hydroxy-2-propyl)-2,6-diisopropylphenyl]-N'-methylurea | 10 |
| Lactose, direct compression grade | 213 |
| Microcrystalline cellulose | 30 |

-continued

| Tablet Formulations | |
|---|---|
| Formulation I | Milligrams per Tablet |
| Sodium Lauryl Sulfate | 20 |
| Corn starch | 25 |
| Magnesium stearate | 2 |
| | 300 |

Mix together the stated active ingredient, lactose, microcrystalline cellulose, sodium lauryl sulfate and corn starch. Pass through a No. 40 screen. Add the magnesium stearate, mix and compress into desired shape on a tablet machine.

| Formulation II | Milligrams per Tablet |
|---|---|
| N-ethyl-N'-[4-(hexafluoro-2-hydroxy-2-propyl)-2,6-diisopropyl-phenyl]-N'-methylurea | 10 |
| Lactose, U.S.P. | 230 |
| Dicalcium phosphate | 58 |
| Sodium Lauryl Sulfate | 20 |
| Polyvinylpyrrolidone | 10 |
| Water 50 ml/1000 tablets | |
| Corn starch | 20 |
| Magnesium Stearate | 2 |
| | 350 |

Mix together the stated active ingredient, lactose, dicalcium phosphate and sodium lauryl sulfate. Screen the above mixture through a No. 60 screen and granulate with an aqueous solution containing polyvinylpyrrolidone. Add additional water, if necessary, to bring the powders to a pasty mass. Add corn starch and continue mixing until uniform granules are formed. Pass through a No. 10 screen, tray and dry in an oven at 40° C for 12 to 14 hours. Reduce the dried granulation through a No. 16 screen. Add magnesium stearate, mix and compress into desired shape on a tablet machine.

EXAMPLE 20

| Capsule Formulations | |
|---|---|
| Formulation I | Milligrams per Capsule |
| N-ethyl-N'-[4-(hexafluoro-2-hydroxy-2-propyl)-2,6-diisopropyl-phenyl]-N'-methylurea | 10 |
| Lactose, U.S.P. | 213 |
| Microcrystalline Cellulose | 30 |
| Sodium Lauryl Sulfate | 20 |
| Corn Starch | 25 |
| Magnesium Stearate | 2 |
| | 300 |

Procedure:

Mix together the stated active ingredient, lactose, microcrystalline cellulose, sodium lauryl sulfate and corn starch. Pass through a No. 80 screen. Add the magnesium stearate, mix and encapsulate into the proper size two-piece gelatin capsule.

What is claimed is:

1. A compound of the formula:

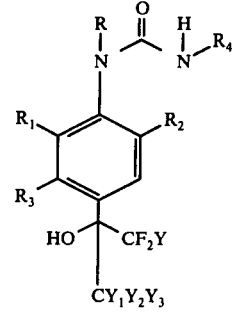

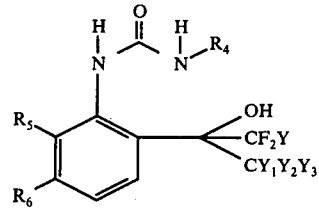

wherein $R_4$ is hydrogen or a methyl, ethyl, 2-chloroethyl or a 2-bromoethyl group;

$R_1$, $R_2$ and $R_3$ are independently hydrogen, fluorine, chlorine, bromine, aminocarbonyl, lower alkyl, lower alkoxy, lower alkoxycarbonyl, hydroxy lower alkyl or nitro;

Y, $Y_1$, $Y_2$ and $Y_3$ are independently hydrogen, fluorine or chlorine;

R is hydrogen, alkyl having 1 to 4 carbon atoms, lower alkoxy lower alkyl or lower dialkoxy lower alkyl;

$R_5$ and $R_6$ are hydrogen or a lower alkyl group or $R_5$ and $R_6$ together complete a 5 or 6 carbon fused hydrocarbon ring which may be saturated or aromatic and which may be optionally substituted by a lower alkyl group.

2. A compound according to claim 1 wherein R is an alkyl group of 1 to 4 carbon atoms.

3. A compound according to claim 1 wherein $R_1$, $R_2$ and $R_3$ are hydrogen.

4. A compound according to claim 1 wherein $R_1$ and $R_2$ are each a lower alkyl group.

5. A compound according to claim 1 wherein $R_5$ and $R_6$ together are a fused cyclohexyl ring.

6. A compound according to claim 1 wherein $R_5$ and $R_6$ together are a fused benzoid ring.

7. A compound according to claim 1 wherein Y, $Y_1$, $Y_2$ and $Y_3$ are each fluorine.

8. A compound according to claim 1 which is N-ethyl-N'-[4-(hexafluoro-2-hydroxy-2-propyl)-2,6-diisopropylphenyl]-N'-methylurea.

9. A compound according to claim 1 which is N-ethyl-N'-methyl-N'-[4-(1,3-dichloro-2-hydroxytetrafluoro-2-propyl)phenyl]urea.

10. A compound according to claim 1 which is N-ethyl-N'-[4-(hexafluoro-2-hydroxy-2-propyl)-2-(ethoxycarbonyl)phenyl]urea.

11. A compound according to claim 1 which is N-(2-chloroethyl)-N'-[4-(hexafluoro-2-hydroxy-2-propyl)-phenyl]-N'-methylurea.

12. A compound according to claim 1 which is N'-(2,2-dimethoxyethyl)-N'-[4-(hexafluoro-2-hydroxy-2-propyl)phenyl]-N-ethylurea.

13. A compound according to claim 1 which is N-ethyl-N'-methyl-N'-[2,6-dimethyl-4-(hexafluoro-2-hydroxy-2-propyl)phenyl]urea.

14. A compound according to claim 1 which is N-[2-(hexafluoro-2-hydroxy-2-propyl)-5,6,7,8-tetrahydro-1-naphthyl]-N'-methylurea.

15. A compound according to claim 1 which is N-ethyl-N'-[2-(hexafluoro-2-hydroxy-2-propyl)-1-naphthyl]urea.

16. A pharmaceutical composition adapted to treat hypertension comprising an oral dosage form of an effective anti-hypertensive amount of a compound of claim 1, in a pharmaceutically acceptable diluent.

17. A composition according to claim 16 in the form of a solid oral dosage unit.

18. A composition according to claim 16 wherein said compound is N-ethyl-N'-[4-(hexafluoro-2-hydroxy-2-propyl)-2,6-diisopropylphenyl]-N'-methylurea.

19. A method of treating hypertension comprising administering to a hypertensive mammal a composition of claim 16.

20. A method according to claim 19 wherein said composition comprises N-ethyl-N'-[4-(hexafluoro-2-hydroxy-2-propyl)-2,6-diisopropylphenyl]-N'-methylurea.

* * * * *